United States Patent [19]

Welch et al.

[11] Patent Number: 5,113,001

[45] Date of Patent: May 12, 1992

[54] PROCESS FOR PREPARING SULFOPHENYLALKYLSILOXANES OR SULFONAPHTHYLALKYLSILOXANES

[75] Inventors: Michael C. Welch, Woodhaven; Rudolph E. Lisa, Grosse Ile; Joe C. Wilson, Woodhaven, all of Mich.

[73] Assignee: BASF Corporation, Parsippany, N.J.

[21] Appl. No.: 742,774

[22] Filed: Aug. 8, 1991

[51] Int. Cl.$^5$ .............................. C07F 7/08
[52] U.S. Cl. ................................ 556/428
[58] Field of Search ........................ 556/428

[56] References Cited

U.S. PATENT DOCUMENTS 2,955,128 10/1960 Bailey ................................. 556/428
4,575,559 3/1986 Pauck et al. ......................... 556/428

*Primary Examiner*—Paul F. Shaver

[57] ABSTRACT

This invention relates to a process for preparing a sulfophenylalkylsiloxane or a sulfonaphthylalkylsiloxane having either of the following formulae:

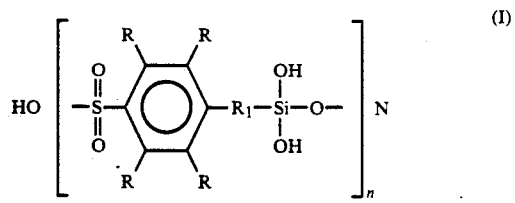

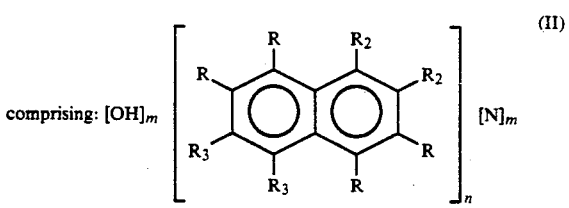

(a) adding an essentially equimolar ratio of chlorosulfonic acid to a phenylalkyltrichlorosilane or a naphthylalkyltrichlorosilane having either of the following formulae:

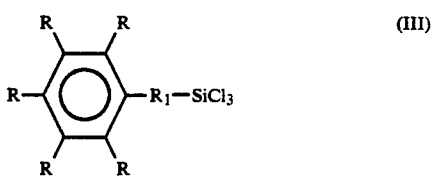

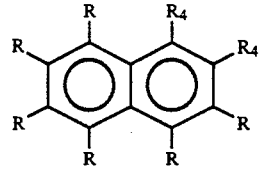

wherein R of formulae I, II, III, and IV is individually hydrogen, halogen, or an alkyl radical having 1 to 4 carbon atoms; $R_1$ is an alkylene radical having 2 to 5 carbon atoms; $R_2$ is R or

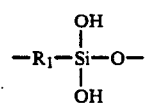

with the proviso that at least one $R_2$ be

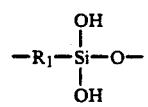

$R_3$ is —H or

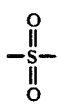

with the proviso that at least one $R_3$ be

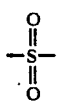

$R_4$ is R or —$R_1SiCl_3$ with the proviso that at least one $R_4$ be —$R_1SiCl_3$ and
n is at least 1,
m is 1 or 2,
in the presence of thionyl chloride at a temperature of from about 0° to about 100° C.;
(b) reacting the reaction mixture at said temperature until the evolution of hydrogen chloride is substantially complete;
(c) removing the volatiles to form a liquid intermediate; and
(d) hydrolyzing said intermediate with water.

The new process avoids solid formation of an intermediate product.

15 Claims, No Drawings

PROCESS FOR PREPARING SULFOPHENYLALKYLSILOXANES OR SULFONAPHTHYLALKYLSILOXANES

FIELD OF THE INVENTION

The present invention is directed to an improved process for preparing certain sulfophenylalkylsiloxanes or sulfonaphthylalkylsiloxanes, more specifically to a process comprising the reaction of chlorosulfonic acid with certain phenylalkyltrichlorosilanes or naphthylalkyltrichlorosilanes in the presence of thionyl chloride.

BACKGROUND OF THE INVENTION

Sulfophenylalkylsiloxanes and processes for their production are known. The U.S. Pat. No. 2,968,643 describes a reaction of chlorosulfonic acid and a phenethyltrichlorosilane to form an intermediate followed by hydrolysis of this intermediate. However, the by-product sulfuric acid resulting from the required excess of chlorosulfonic acid has to be separated. The U.S. Pat. No. 4,575,559 discloses a process for the production of sulfophenethylsiloxane in the presence or absence of solvent. The solventless process in a stirred vessel is very difficult to process because the reaction mixture becomes solid.

The object of the present invention was to provide a process for the production of sulfophenylalkylsiloxane or sulfonaphthylalkylsiloxanes which avoids solid intermediates formation and the formation of difficult to separate by-products and can be carried out in a conventional reactor system.

SUMMARY OF THE INVENTION

The object of the present invention could be achieved with a process for preparing a sulfophenylalkylsiloxane or sulfonaphthylalkylsiloxanes having either of the following formulae:

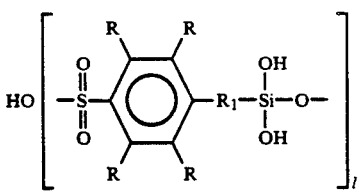

comprising:

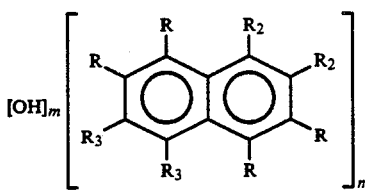

(a) adding an essentially equimolar ratio of chlorosulfonic acid to a phenylalkyltrichlorosilane or naphthylalkyltrichlorosilane having either of the following formulae:

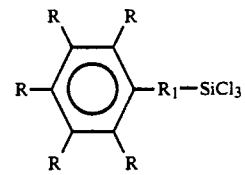

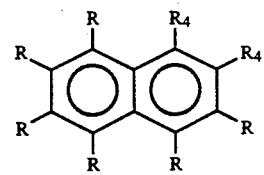

wherein R of formula I, II, III, and IV is individually hydrogen, halogen, or an alkyl radical having 1 to 4 carbon atoms; $R_1$ is an alkylene radical having 2 to 5 carbon atoms; $R_2$ is R or

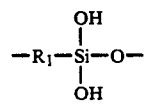

with the proviso that at least one $R_2$ be

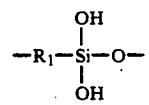

$R_3$ is —H or

with the proviso that at least one $R_3$ be

$R_4$ is R or $-R_1SiCl_3$ with the proviso that at least one $R_4$ be $-R_1SiCl_3$ and
n is at least 1,
m is 1 or 2 in the presence of thionyl chloride at a temperature of from about 0° to about 100° C.;

(b) reacting the reaction mixture at said temperature until the evolution of hydrogen chloride is substantially complete;
(c) removing the volatiles to form a liquid intermediate; and
(d) hydrolyzing said intermediate with water.

DETAILED DESCRIPTION OF THE INVENTION

The phenylalkyltrichlorosilane and naphthylalkyltrichlorosilane compounds having structural formula III and IV are well known in the art and are described, for example, in U.S. Pat. No. 2,955,128. R is hydrogen, halogen or an alkyl radical having 1–4 carbon atoms, $R_1$ is an alkylene radical having 2 to 5 carbon atoms and $R_4$ is R or $—R_1SiCl_3$ with the proviso that at least one $R_4$ be $—R_1SiCl_3$. Suitable examples of these compounds are alpha-phenylethyltrichlorosilane, beta-phenylethyltrichlorosilane, betaphenylpropyltrichlorosilane, gamma-phenylpropyltrichlorosilane, beta-naphthylethyltrichlorosilane and the like.

In step (a) of the process for preparing the sulfophenylalkylsiloxane or sulfo-naphthylalkylsiloxane the phenylalkyltrichlorosilane or naphtyl-alkyltrichlorosilane is introduced into a conventional reaction vessel together with thionyl chloride. The thionyl chloride is used in a sufficient amount to inhibit solid intermediates formation. Usually from about 10 mols, preferably about 1.2 to about 5 mols, most preferred about 1 5 to about mols of thionyl chloride, per mol phenylalkyltrichlorosilane or naphtylalkyltrichlorosilane is used. The chlorosulfonic acid is added slowly over a time period of from about 1 to 6 hours, preferably 2 to 4 hours, to the reaction mixture which is at a temperature of from about 0° to 100° C., preferably 60° to 80° C., and after the addition is completed the reaction in step (b) is held for about 1 to about 3 hours at this temperature. Steps (a) and (b) could be optionally performed in an autoclave under elevated pressure. Thereafter, the evolution of hydrogen chloride is substantially complete.

It is important that the hydrogen chloride evolution is complete because otherwise insoluble by-products are likely to form.

The molar ratio of the phenylalkyltrichlorosilane or naphtylalkyltrichlorosilane to chlorosulfonic acid is from about 0.8 to about 1.1:1, preferably from about 0.95 to about 1.0:1.

The volatiles are removed in step (c) from the reaction by distillation, preferably under reduced pressure.

The resulting intermediate is surprisingly in a liquid form, in contrast to the solid reaction mass of the processes of the Prior Art.

The hydrolysis in step (d) is achieved by adding the liquid intermediate to an excess of distilled water of a temperature from about 0° to about 25° C., preferably 0° to about 10° C. to form a solid, which is filtered and washed with water.

The resulting solid is heated in the presence of water to a temperature of from about 50° to about 100° C. in order to complete the hydrolysis and is then dried.

In order to eliminate all remaining chloride from the solid, the hydrolysis could be repeated until no chloride could be detected followed by drying the resulting solid.

The final dry powder is a sulfophenylalkylsiloxane or a sulfonaphthylalkylsiloxane.

The yield in this process is high and is usually of more than 98 percent without significant amounts of environmentally undesired by-products.

The product is used for example in antifreeze formulations in amounts effective as a silicate stabilizer.

In an alternative hydrolysis step (d) an organic solvent, which is stable under the hydrolysis conditions like an aliphatic or cycloaliphatic hydrocarbon, preferably a $C_{10}$ to $C_{20}$ aliphatic hydrocarbon, is added to the liquid intermediate of step (c) followed by adding distilled water. The mixture is heated to a temperature of from about 50° to about 150° C., optionally in an autoclave under elevated pressure. After the hydrolysis the water is removed by distillation to form a suspension of a solvent in the organic solvent.

The organic solvent is used in an amount to provide a suspension. In order to eliminate all remaining chloride, water could be added and removed again or as an alternative steam could be passed through the suspension until no more chloride is detectable.

The resulting hydrolysis product may be isolated by removing the organic solvent or may be extracted in step (e) from the organic solvent by an aqueous base like caustic soda (sodium hydroxide) to form an aqueous solution of a metal salt of sulfophenylalkylsiloxane or sulfonaphthylalkylsiloxane, which could be used in antifreeze formulation as well.

EXAMPLE 1

To a suitable reaction vessel containing 106.6 grams betaphenylethyltrichlorosilane and 106.6 grams thionyl chloride at 80° C. was added 52.0 grams chlorosulfonic acid slowly dropwise over 230 minutes. After an additional two hours reaction time, volatiles were removed under vacuum. The residue was poured into cold water and the resulting precipitate recovered by filtration. Water was added to the solid and the mixture was heated to 100° C. to complete the hydrolysis and evaporated to dryness. The hydrolysis was repeated until no chloride could be detected using silver nitrate. Spectral and physical characterization identified the product as beta-sulfophenylethylsiloxane.

EXAMPLE 2

To a suitable stirred reaction vessel, 11.25 lbs of thionyl chloride and 11.12 lbs of beta-phenylethyltrichlorosilane were added. The stirred mixture was heated to 80° C., and 5.43 lbs of chlorosulfonic acid were added over a 230 minute period. The reaction was maintained for an additional 2 hours at 80° C., and then the volatiles were removed under vacuum. For the hydrolysis, 170 grams of the intermediate from the above reaction and 300 grams of a C-12 cut of aliphatic hydrocarbon were added to a suitable reaction vessel. 60 grams of distilled water was added slowly and the stirred mixture heated to 107° C. The volatiles leaving the reactor were passed through a condenser, and the condensed fraction trapped in a Stark trap, with any carryover hydrocarbon being refluxed. When the evolution of volatiles subsided, steam was sparged into the vessel for three hours. After sparging, the water was removed under vacuum, the mixture was cooled, and the resultant product extracted and separated with a 10% by weight aqueous caustic soda solution.

What is claimed is:

1. A process for preparing a sulfophenylalkylsiloxane or a sulfonaphthylalkylsiloxane having either of the following formulae:

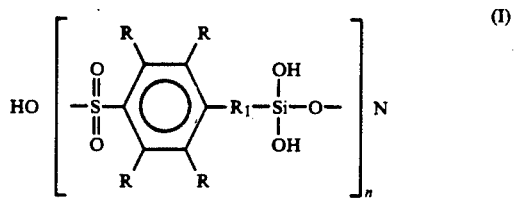

comprising: $[OH]_m$ 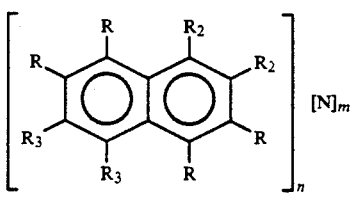 $[N]_m$ (a) adding an essentially equimolar ratio of chlorosulfonic acid to a phenylalkyltrichlorosilane or a naphthylalkyltrichlorosilane having either of the following formulae:

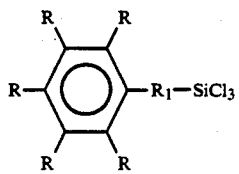

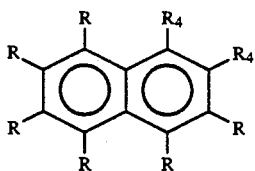

wherein R of formulae I, II, III, and IV is individually hydrogen halogen, or an alkyl radical having 1 to 4 carbon atoms; $R_1$ is an alkylene radical having 2 to 5 carbon atoms; $R_2$ is R or

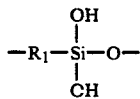

with he proviso that at least one $R_2$ be

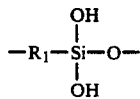

$R_3$ is —H or

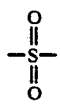

with the proviso that at least one $R_3$ be

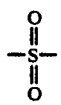

$R_4$ is R or $-R_1SiCl_3$ with the proviso that at least one $R_4$ be $-R_1SiCl_3$ and n is at least 1, m is 1 or 2, in the presence of thionyl chloride at a temperature of from about 0° to about 100° C.;

(b) reacting the reaction mixture at said temperature until the evolution of hydrogen chloride is substantially complete;

(c) removing the volatiles to form a liquid intermediate; and (d) hydrolyzing said intermediate with water.

2. The process according to claim 1, wherein from about 1 to about 10 mols thionyl chloride is used per mol phenylalkyltrichlorosilane or naphthylalkyltrichlorosilane in step (a).

3. The process according to claim 1, wherein the molar ratio of the phenylalkyltrichlorosilane or naphthylalkyltrichlorosilane to chlorosulfonic acid is from about 0.8 to about 1.1:1.

4. The process according to claim 1, wherein the chlorosulfonic acid in step (a) is added over a time period of from about 1 hour to 6 hours.

5. The process according to claim 1, wherein the temperature in step (a) and (b) is from about 60° C. to about 80° C.

6. The process according to claim 1, wherein the volatiles in step (c) are removed under reduced pressure.

7. The process according to claim 1, wherein n is 2 to 3.

8. The process according to claim 1, wherein said intermediate is hydrolyzed in step (d) at a temperature of from about 50° to about 100° C.

9. The process according to claim 1, wherein said phenylalkyltrichlorsilane is selected from the group consisting of alphaphenylethyltrichlorosilane, beta-phenylethyltrichlorosilane, betaphenylpropyltrichlorosilane and gamma-phenylpropyltrichlorosilane.

10. The process according to claim 1, wherein said phenylalkyltrichlorosilane is beta-phenylethyltrichlorosilane.

11. The process according to claim 1, wherein said naphthylalkyltrichlorosilane is beta-naphthylethyltrichlorosilane.

12. The process according to claim 1, wherein the hydrolyzing step (d) is performed with water in the presence of an organic solvent, which is stable under the hydrolysis conditions at a temperature of from about 50° to about 150° C. to form a suspension.

13. The process according to claim 12, wherein said solvent is selected from the group consisting of an aliphatic hydrocarbon, cycloaliphatic hydrocarbon and mixtures thereof.

14. The process according to claim 13, wherein said aliphatic hydrocarbon is a $C_{10}$-$C_{20}$ hydrocarbon.

15. The process according to claim 12, further comprising:

(e) extracting said suspension with an aqueous base to form an aqueous solution of a metal salt of sulfophenylalkylsiloxane or sulfonaphthylalkylsiloxane.

* * * * *

UNITED STATES PATENT AND TRADEMARK OFFICE
CERTIFICATE OF CORRECTION

PATENT NO. : 5,113,001
DATED : May 12, 1992
INVENTOR(S) : Michael Welch, Rudolph Lisa, Joe Wilson It is certified that error appears in the above-indentified patent and that said Letters Patent is hereby corrected as shown below:

Formula (I) and (II) in the Item [57], in column 1, and in claim 1 should appear as follows:

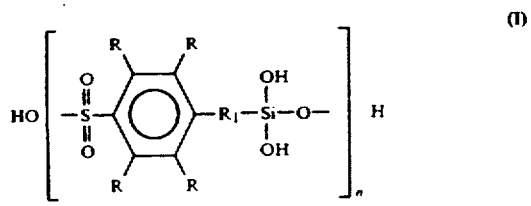

(I)

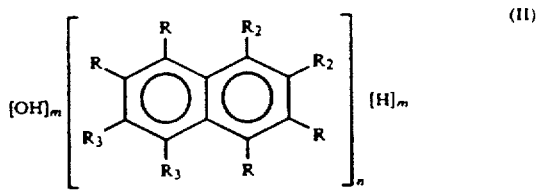

(II)

Signed and Sealed this

Twenty-first Day of June, 1994

*Attest:*

BRUCE LEHMAN

*Attesting Officer*     Commissioner of Patents and Trademarks